United States Patent
You-Min et al.

(10) Patent No.: US 6,800,606 B1
(45) Date of Patent: Oct. 5, 2004

(54) MONOMERIC ANALOGUES OF HUMAN INSULIN

(75) Inventors: Feng You-Min, Shanghai (CN); You-Shang Zhang, Shanghai (CN)

(73) Assignee: Shanghai Institute of Biochemistry (CN)

( * ) Notice: Subject to any disclaimer, the term of this patent is extended or adjusted under 35 U.S.C. 154(b) by 76 days.

(21) Appl. No.: 10/070,568

(22) PCT Filed: Sep. 8, 2000

(86) PCT No.: PCT/GB00/03460

§ 371 (c)(1),
(2), (4) Date: Mar. 8, 2002

(87) PCT Pub. No.: WO01/18052

PCT Pub. Date: Mar. 15, 2001

(30) Foreign Application Priority Data

Sep. 8, 1999 (CN) ...................... 99 1 16851.8

(51) Int. Cl.[7] .......................... A61K 38/28; C07K 14/62
(52) U.S. Cl. ............................... 514/3; 514/2; 530/303; 530/304; 530/305
(58) Field of Search ........................ 514/2, 3; 530/303, 530/304, 305

(56) References Cited

U.S. PATENT DOCUMENTS

| | | |
|---|---|---|
| 4,916,212 A | 4/1990 | Markussen et al. |
| 5,618,913 A | 4/1997 | Brange et al. |
| 5,952,297 A | 9/1999 | De Felippis et al. |

FOREIGN PATENT DOCUMENTS

| | | |
|---|---|---|
| CN | 93112588.3 | 4/1993 |
| EP | 0 046 979 A | 3/1982 |
| EP | 0 214 826 A2 | 3/1987 |
| EP | 0 291 863 A | 11/1988 |
| WO | WO 94/14461 * | 7/1994 |

OTHER PUBLICATIONS

Kristensen et al. 'Alanine Scanning Mutagenesis of Insulin', The Journal of Biological Chemistry 272(20), pp. 12978–12983. May 1997.*

Slieker et al. Modification in the B10 and B26–B30 Regions of the B Chain of Human Insulin Alter Affinity for the Human IGF–1 Receptor Mroe than for the Insulin Receptor. Diabetologia, vol. 40, pp. s54–s61, 1997.*

Brange, J. et al. (Jun. 16, 1988) "Monomeric insulins obtained by protein engineering and their medical implications" *Nature* (London) 333:679–682.

Jensen, Ivan et al. (1991) "Scintigraphic studies in rats: kinetics of insulin analogs covering wide range of receptor affinities" *Chemical Abstracts Service*, Database accession No. 115:224155CA (Diabetes, 1991, 40(5): 628–32) abstract only.

Kristensen, Claus et al. (May 16, 1997) "Alanine Scanning Mutagenesis of Insulin" *The Journal of Biological Chemistry* 272(20):12978–12983.

Noble, Sara L., Elizabeth Johnston, Bill Walton (Jan. 15, 1998) "Insulin Lispro: A Fast–Acting Insulin Analog" In: *The American Academy of Family Physicians*.

Wang, Qiong–Qing et al. (Nov. 18, 1996) "Studies on receptor binding site of insulin: the hydrophobic B12Val can be substituted by hydrophilic Thr" *Chemical Abstracts* 125(21), abstract No. 266145 (Biochem. Mol. Biol. Int. 39(6):1245–1254) abstract only.

\* cited by examiner

*Primary Examiner*—Brenda Brumback
*Assistant Examiner*—Anish Gupta
(74) *Attorney, Agent, or Firm*—Saliwanchik, Lloyd & Saliwanchik

(57) ABSTRACT

Monomeric analogues of human insulin have a single substitution of the amino acid in 12th, 16th or the 26th position of the B chain of human insulin and may also have a terminal deletion in the B chain.

10 Claims, 1 Drawing Sheet

MONOMERIC ANALOGUES OF HUMAN INSULIN

This application is a National Stage Application of International Application Number PCT/GB00/03460, published, pursuant to PCT Article 21(2), in English.

FIELD OF THE INVENTION

This invention relates to novel monomeric analogues of human insulin (HI) obtainable by recombinant DNA technology.

BACKGROUND OF THE INVENTION

Insulin is highly effective in treating insulin-dependent diabetes, and has been used clinically for nearly 80 years. With advances in DNA technology and the development of biotechnology industries, insulin extracted from animal pancreas is gradually being replaced by recombinant forms of human insulin, produced in microbial systems. This trend is encouraged by two observations, the number suffering from diabetes mellitus is on the increase globally and the clinical dose required to treat them is in milligram (mg) quantities.

Currently, the organisms employed for the commercial production of recombinant human insulin are *E. coli* and *S. cerevisiae*. The expression levels in *E. coli* are high but difficulties associated with downstream purification often lead to loss of yield. These difficulties are not encountered with *S. cerevisiae*, because the insulin produced is secreted into the culture medium, facilitating purification. However, the level of expression observed in this organism is low and difficult to increase.

Until recently, introduction of Lispro®, clinical preparations of human insulin contained polymeric forms of insulin which are slow acting. Monomeric forms of insulin, as described in U.S Pat. No. 5618913, by contrast, are relatively fast-acting and mimic more closely the natural situation. They therefore demonstrate a great potential for clinical application. A commercial monomeric insulin, available as Lispro®, comprises inversion of amino acids 28 and 29 of the B chain of human insulin, and may be abbreviated as B28Lys,B29Pro.

Kristensen et al, J. Biol. Chem. 272(20):12978-83 (1997), discloses alanine substitution at various positions on the insulin molecule, including B12, B16 and B26. A single substitution with Ala affected the binding activity of the resultant insulin analogue in certain cases.

Wang et al, Biochem. Mol. Biol. Int. 39(6):1245-54 (1996), discloses B12Thr, i.e. an insulin analogue in which the $12^{th}$ amino acid of the B-chain of human insulin (Val) is substituted by Thr. Again, an effect on binding activity was observed.

EP-A-0046979 discloses des-B30 derivatives of human insulin.

EP-A-0291863 discloses des-B1 derivatives of human insulin.

SUMMARY OF THE INVENTION

According to the present invention, novel human insulin analogues are monomeric variants of B12Thr, B16Ala and B26Ala; the latter have not previously been recognised as monomeric. In addition to replacement of any or all of the $12^{th}$, $16^{th}$ and $26^{th}$ amino acids on the B-chain, such that the analogue is monomeric, the B-1 and/or B-30 terminal amino acids may be absent. The term "insulin analogue" as used herein means a compound having a molecular structure similar to that of human insulin, including disulphide bridges between A7Cys and B7Cys and between A20Cys and B19Cys, and an internal disulphide bridge between A6Cys and A11Cys, and having insulin activity.

Without wishing to be bound by theory, it appears that, in the primary structure of the insulin molecule, a number of the amino acids in the B-chain are responsible for the polymerisation of insulin in clinical preparations. These include those in positions B12, B16 and B26. In particular, the replacement of Val by Thr in position B12 or Tyr by Ala in position B16 or B26 significantly reduces the tendency of the insulin analogues to polymerise even at high concentrations (see Example 9). This enhanced tendency to exist as a monomeric structure is not affected by deletion of either one or both of the terminal amino acids of the B-chain.

DESCRIPTION OF THE INVENTION

The Scheme, below, shows the construction of the expression plasmids pNHI-2/AOX1, pNHI-3/AOX1, pNHI4/AOX1 and the engineering of recombinant cells YP99/NHI-2, YP99/NHI-3 and YP99/NHI-4. It sets out a representative procedure for the preparation of compounds of the invention, by analogy with the use of the human insulin target gene (HI) housed in the shuttle plasmid pHI/PGK. This shuttle vector is constructed from the plasmid pVT102-U (acquired from Canadian Research Institute) and subsequently multiplied by PCR (Maniatis et al (1989), Molecular Cloning A Laboratory Manual, $2^{nd}$ ed. New York: Cold Spring Harbour Laboratory), to obtain multiple copies of human insulin target gene (HI) and flanking alpha mating factor leader (MFL) sequence. The target gene is then cloned into plasmid pPIC9 which is subsequently linearised with BglII prior to being employed to transform *P. pastoris* cell GS115 by the spheroplast method. Once plasmid pPIC9 containing the target gene is internalised, it integrates into the chromosomal DNA of the host cell [1]. Transformed cells bearing a high copy number of the HI gene are selected using the antibiotic G418 by the method described by Scover et al [2]. The presence of multiple copies of the HI are ascertained by the dot blotting method [3]. Cells bearing a high copy number of the HI gene are utilised to generate the human insulin precursor by fermentation, and after purification converted to human insulin by tryptic transpeptidation.

In order to obtain recombinant forms of human insulin analogues according to this invention, target genes were produced. This was accomplished by the "gap double-stranded DNA" method described by Li Yiping et al. (1987*Biotech*. J. 3:90) which permits site-directed mutations in the HI target gene. Primers specifically designed to give B12Thr, B16Ala and B26Ala were as follows; For B12Thr (NHI-2): refer to Wang et al., *supra* For B16Ala (NHI-3): 5' TGA GGC TTT GNN STT GGT TTG CG 3' (SEQ ID No.1) in which N can be any nucleotide (G,A,T or C), and S is C or G. For B26Ala (NHI-4): 5' GAA AGA GGTT TTC NNS ACT CCT AGG GC 3' (SEQ ID No.2) in which N and S are as defined above.

Novel human insulin analogues may be obtained by removing B30Thr and/or B1Phe, e.g. yielding a des-B1 and/or des-B30 analogue. Deletion may be achieved by known methodology. Rather than tryptic transpeptidation, to produce des-B30 human insulin, limited hydrolysis has been adopted, using trypsin in the preferred method, which further simplifies the process and increases the yield of insulin.

The methylotrophic yeast, *Pichia pastoris* is the preferred host for use In this invention for the preparation of insulin analogues because, as the Examples show, it has the advantages of high expression, simple processing, low production cost and high density culture. Furthermore it offers the advantages of a eukaryotic cell system; the correct folding and post-translational processing of secreted protein These advantages greatly enhance the possibility of utilizing *P. pastoris* as the expression host in the scale-up of human insulin production. Its use in the expression of proteins of commercial importance has been documented elsewhere [3–5].

Human insulin analogues of the invention may be used in therapy. Their application and utility will be readily evident to those of ordinary skill in the art, e.g. in the treatment of diabetes mellitus.

Figure 1:
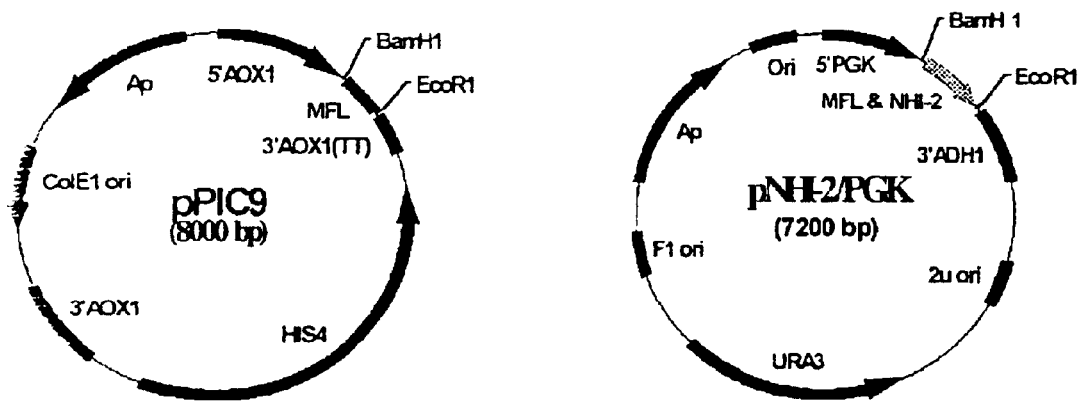
FIG. 1 shows the construction of pNHI2/AOX1 plasmid of *Pichia pastoris*.
Figure 1:
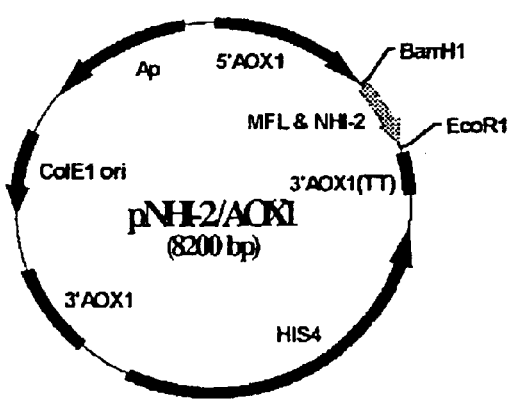

The following Examples illustrate the invention.

EXAMPLE 1

Cloning of Mutated HI Gene

The plasmid pVT102-U from Canadian Biotechnology Research Institute was used to construct the plasmid pHI/PGK according to the standard method described in Maniatis et al (1989). The construct pHI/PGK is a shuttle plasmid with phosphoglycerate kinase (PGK) promoter, followed by alpha mating factor leader sequence (MFL) to direct secretion of the product of the human insulin target gene (HI) flanked by a BamHI site at MFL 5' end and a HindIII site at HI 3' end. Using pHI/PGK as template, together with TCCGGATCCATGAGATTT (SEQ ID NO. 3) as the 5' primer and TGAATTCTTCTAGTTGCAGTAGTTT (SEQ ID NO. 4) as the 3' primer, DNA fragments containing MFL and HI with the BamHI site GGATCC at 5' end and the EcoR1 site GAATTC at the 3' end were obtained by PCR. To obtain DNA fragments containing MFL and the target gene NHI-2 (B12Thr), NHI-3 (B16Ala) and NHI-4 (B26Ala) the HI target gene in pHI/PGK plasmid was first mutated by site-directed mutagenesis then replicated by PCR. By inserting these fragments behind the AOX1 promoter of the plasmid pPIC9 (Invitrogen), expression plasmids pNHI-2/AOX1, pNHI-3/AOX1 and pNHI-4/AOX1 were obtained (see the Scheme and the accompany drawing; the latter shows the first plasmid, and the others may be prepared by the same procedure). The primers used to obtain the mutated genes in this invention have SEQ ID NOS. 1, 2 and 3.

EXAMPLE 2

Construction and Screening of Expression Cell

The expression plasmids were linearised by BglII and used to transform *P. pastoris* cell GS115 (Invitrogen) using the spheroplast method. The linearised plasmids, once internalized, integrate into the chromosomal DNA of the host cell [1]. The recombinant cells, designated YP99/NHI-2, YP99/NHI-3 and YP99/HNI-4 with high copy number of the target gene, were selected by antibiotic G418 [2] and identified by the dot blotting method [3].

EXAMPLE 3

Preparation of Precursors of HI analogues

High density fermentation was carried out in a 15 litre fermenter [7]. The following salt solutions were used in the fermentation: BSM-$H_3PO_4$ 26.7 ml/l, $CaSO_4.H_2O$ 0.93 g/l, $K_2SO_4$ 18.2 g/l, $MgSO_4.7H_2O$ 14.9 g/l, KOH 4.13 g/l; PTM1 -$CuSO_4$. $5H_2O$ 6 g/l, KI 0.08 g/l, $MnSO_4H_2O$ 3.0 g/l, $NaMoO_4.H_2O$ 0.2 g/l, $H_3BO_3$ 0.02 g/l, $CoCl_26H_2O$ 0.5 g/l, $ZnSO_4$ 20.0 g/l, $H_2SO_4$ 5 ml/l, $FeSO_4.7H_2O$ 65.0 g/l.

Fermentation medium containing 6 L of salt solution BSM and 300 ml of glycerol is sterilised in the fermenter. Its pH is adjusted to 5.5 with 50% ammonium hydroxide. A 5 ml aliquot of salt solution PTM1 containing 1 mg of biotin is added per 1 litre of culture medium. The expression cell is inoculated to 50 ml YPG and grown in a shake flask at 30° C. for 24 hr. The broth is added to 600 ml of YPG, shaken in 3 flasks for 24 hr, added to the culture medium and fermented for 24 hr to deplete glycerol. Methanol solution containing PTM1 (5 ml/l) and biotin (1 mg/l) is added to induce the expression. The inductive fermentation is continued for 84 hr by feeding the above methanol solution. During the fermentation, the pH is maintained at 5.5 by adding 50% ammonium hydroxide. The expression level is measured by radioimmunoassay, SDS-polyacrylamide gel electrophoresis [8] and HPLC.

EXAMPLE 4

Separation and Purification of the Precursors

The fermentation broth is centrifuged to remove the cell bodies. The supernatant is applied to a C8 column and purified by HPLC. After a single step of purification, a product can be obtained that is homogeneous in native polyacrylamide gel electrophoresis.

EXAMPLE 5

Transpeptidation of the Precursors

Purified precursors of HI analogues from Example 4 are dissolved in DMSO/1,4-butanediol/$H_2O$ (15:70:15, v/v) to a concentration of 30 mg/ml. Thr($Bu^t$)-$OBu^t$ is added in excess, and the pH is adjusted to 6.5 by ammonium hydroxide. TPCK-trypsin is added (substrate:enzyme=5:1) and the reaction mixture is incubated at 25° C. for 6 hr. The reaction is stopped by acidification. The product is precipitated using acetone, and purified by HPLC using C8 column.

EXAMPLE 6

Preparation of des-B30 analogues

Purified precursors of HI analogues are dissolved in pH 8, 0.1M ammonium bicarbonate to a concentration of 10 mg/ml. TPCK-trypsin is added (substrate:enzyme=200:1) and the reaction mixture is incubated at 25° C. overnight. The product is analysed by native polyacrylamide gel electrophoresis

EXAMPLE 7

Preparation of Des-B1 analogues

HI analogues are reacted with phenylisocyanate in a molar ratio of 1:2, prior to treatment with trifluoroacetic acid as described by Bradenburg & Hoppe-Seyler, Physiol. Chem. 350:471. The products of this reaction are separated and analysed by electrophoresis and found to be almost exclusively des-B1 forms of insulin analogues.

EXAMPLE 8

Preparation of Des-B1, Des-B30 analogues

Prepared by processing precursors of HI analogues as described in Example 6 followed sequentially by that described in Example 7.

EXAMPLE 9

Determination of Structural Forms

The structural form of the recombinant human insulin analogues prior to deletion of the one or both terminal amino acids of the B-chain is determined electrophoretically. A preparation of each analogue is passed through Superdex G-75 column (HR 10/30). HI and [B28Lys, B29Pro] insulin (Lispro) are used as negative and positive controls respectively. Phosphate buffered saline pH 7.4 is used as an elution buffer and the flow rate fixed at 0.4 ml/min. The concentration of the sample preparation is 1.2 mg/ml. The retention times and the peak profiles of human insulin analogues are shown in the following Table.

| Sample | Retention Time, min | Peak profile |
|---|---|---|
| HI | 36.4 | Unsymmetrical |
| [B28Lys, B29Pro]HI | 39.4 | Symmetrical |
| [B12Thr]HI | 39.4 | Symmetrical |
| [B16Ala]HI | 38.3 | Symmetrical |
| [B26Ala]HI | 38.9 | Symmetrical |

These results demonstrate that HI analogues B12Thr, B16Ala and B26Ala are all monomeric in form. They have a similar retention time and peak profile as the known positive control [B28Lys, B29Pro] human insulin.

References

1. Cregg et al (1985), Mol. Cell. Biol. 5:3376
2. Scover et a/ (1994), Bio/Technology 12:181
4. Hagenson et al (1989), Enzy. Micro. Tech. 11:650
5. Steinlein et al (1995), Prot. Exp. Pur. 6:619
3. Clare et al(1991), Gene 105:205
6. Li YiPing et al (1987). Biotech. J. 3:90
7. Laroche et al (1994), Bio/Technology 12:1119
8. Schagger et al (1987), Anal. Biochem. 166:368

Scheme

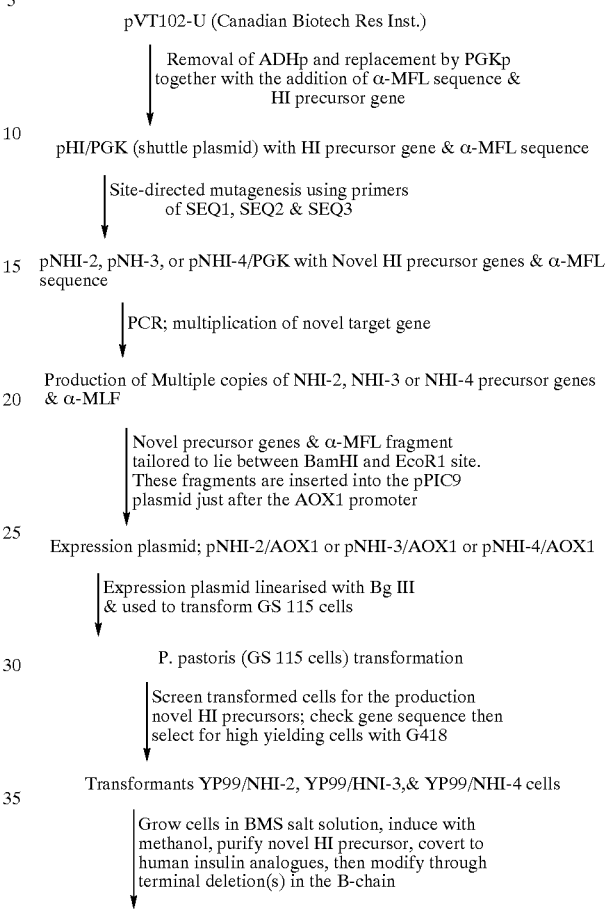

What is claimed is:

1. A method for treating an individual having an insulin deficiency wherein said method comprises administering to the individual an insulin analogue wherein the Tyr at the $16^{th}$ or $26^{th}$ position of the B chain of human insulin is substituted by Ala, and said analogue has a deletion at either one or both of Phe at position 1, B1, or Thr at position 30, B30, of the B-chain of human insulin.

2. The method, according to claim 1, wherein, at the $26^{th}$ amino acid, the analogue is substituted by Ala.

3. The method, according to claim 2, wherein said analogue has a deletion of B30.

4. The method according to claim 1, wherein at the $16^{th}$ amino acid the analogue is substituted by Ala.

5. The method, according to claim 4, wherein said analogue has a deletion at B30.

6. A pharmaceutical composition comprising an insulin analogue wherein the Tyr at the $16^{th}$ or $26^{th}$ position of the B chain of human insulin is substituted by Ala, and said analogue has a deletion at either one or both of Phe at position 1, B1, or Thr at position 30, B30, of the B chain of human insulin wherein said composition further comprises a pharmaceutical carrier.

7. The pharmaceutical composition, according to claim 6, wherein at the $26^{th}$ amino acid, the analogue is substituted by Ala.

8. The pharmaceutical composition, according to claim 7, wherein said analogue has a deletion of B30.

9. The pharmaceutical composition, according to claim 6, wherein at the $16^{th}$ amino acid, the analogue is substituted by Ala.

10. The pharmaceutical composition, according to claim 9, wherein said analogue has a deletion at B30.

* * * * *

```
SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide NHI-3
<220> FEATURE:
<221> NAME/KEY: misc_feature
<222> LOCATION: (11)..(11)
<223> OTHER INFORMATION: n = a, c, g, or t.
<220> FEATURE:
<221> NAME/KEY: misc_feature
<222> LOCATION: (12)..(12)
<223> OTHER INFORMATION: n = a, c, g, or t.
<220> FEATURE:
<221> NAME/KEY: misc_feature
<222> LOCATION: (13)..(13)
<223> OTHER INFORMATION: s = c or g.

<400> SEQUENCE: 1
tgaggctttg nnsttggttt gcg                                             23
```

```
<210> SEQ ID NO 2
<211> LENGTH: 27
<212> TYPE: DNA
<213> ORGANISM: Artificial Sequence
<220> FEATURE:
<223> OTHER INFORMATION: Oligonucleotide NHI-4
<220> FEATURE:
<221> NAME/KEY: misc_feature
<222> LOCATION: (14)..(14)
<223> OTHER INFORMATION: n = a, c, g, or t.
<220> FEATURE:
<221> NAME/KEY: misc_feature
<222> LOCATION: (15)..(15)
<223> OTHER INFORMATION: n = a, c, g, or t.
<220> FEATURE:
<221> NAME/KEY: misc_feature
<222> LOCATION: (16)..(16)
<223> OTHER INFORMATION: s = c or g.

<400> SEQUENCE: 2
gaaagaggtt ttcnnsactc ctagggc                                              27

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide MFL 5' primer

<400> SEQUENCE: 3
tccggatcca tgagattt                                                        18

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide HI 3' primer

<400> SEQUENCE: 4
tgaattcttc tagttgcagt agttt                                                25
```